United States Patent [19]

Ohno et al.

[11] Patent Number: 4,980,347
[45] Date of Patent: * Dec. 25, 1990

[54] PLATINUM COMPLEX, PROCESS FOR PREPARING SAME AND ANTITUMOR AGENT

[75] Inventors: Masaji Ohno; Masato Mutoh, both of Kamakura; Go Hata, Fujisawa; Keiichi Matsunaga, Okazaki; Satoshi Hanada, Ohtsu, all of Japan

[73] Assignee: Toray Industries, Tokyo, Japan

[*] Notice: The portion of the term of this patent subsequent to Mar. 27, 2007 has been disclaimed.

[21] Appl. No.: 337,573

[22] Filed: Apr. 13, 1989

Related U.S. Application Data

[63] Continuation-in-part of Ser. No. 108,074, Oct. 13, 1987, Pat. No. 4,912,100.

[30] Foreign Application Priority Data

Oct. 15, 1986 [JP] Japan .................................. 61-243178
Feb. 19, 1987 [JP] Japan .................................. 62-36720
Mar. 6, 1987 [JP] Japan .................................. 62-50165
Apr. 15, 1988 [JP] Japan .................................. 63-93974

[51] Int. Cl.$^5$ ........................ C07F 15/00; A61K 31/28
[52] U.S. Cl. ................................. 514/186; 514/184; 549/3; 549/210
[58] Field of Search ................... 549/3, 210; 514/184, 514/186

[56] References Cited

U.S. PATENT DOCUMENTS 4,661,516 4/1987 Brown et al. ................... 514/492

*Primary Examiner*—Nicky Chan
*Attorney, Agent, or Firm*—Austin R. Miller

[57] ABSTRACT

A platinum complex represented by the formula:

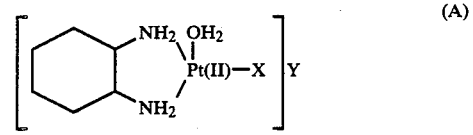

(A)

where X is

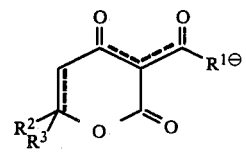

wherein $R^1$ is a (C1–18) alkyl group, a (C1–18)alkenyl group or a group $-Z-R^4$ in which Z is —CH=CH— or a (C1–5)alkylene group, and $R^4$ is a phenyl group, a hydroxyphenyl group, a (C7–12)alkoxyphenyl group, a halogenophenyl group, a nitrophenyl group, or (C8–13-)alkoxycarbonylphenyl group, a cyclohexyl group having a (C1–5)alkyl substituent,

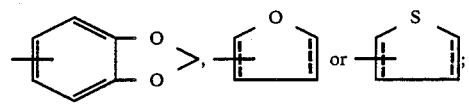

$R^2$ is hydrogen or a (C1–18)alkyl group, $R^3$ is hydrogen or a (C1–3) alkyl group, $R^2$ and $R^3$ are linked together to form a (C2–7)alkylene group; the dotted line indicates that the bond may be either a single bond or a double bond; the chain line indicates a conjugated system; the 1,2-diaminocyclohexane moiety has a cis-, trans-l- or trans-d-configuration; and Y is an anion. This platinum complex is useful in the treatment of tumors.

5 Claims, No Drawings

PLATINUM COMPLEX, PROCESS FOR PREPARING SAME AND ANTITUMOR AGENT

CROSS-REFERENCE TO RELATED APPLICATION

This application is a continuation-in-part of Ser. No. 108,074 filed Oct. 13, 1987, U.S. Pat. No. 4,912,100.

BACKGROUND OF THE INVENTION (1) Field of the Invention

The present invention relates to novel platinum complexes, processes for the synthesis of the same, and pharmaceutical compositions for the treatment of malignant tumors which contains the same as the active ingredient.

(2) Description of the Related Art

The clinical application of cis-diamminedichloroplatinum (II) (hereinafter referred to as "CDDP") has recently brought marked progress in the chemotherapy of malignant tumors. Namely, CDDP shows a high antitumor activity towards cancers of sexual organs such as ovary and testis. However, in clinical use, CDDP causes serious problems due to severe adverse effects including toxic effects on the kidney and the bone marrow. In this connection, renal toxicity is generally considered to be a dose-limiting factor (DLF) in the clinical use of CDDP, and thus, a number of studies have been carried out to reduce the renal toxicity or to seek other platinum complexes with a reduced toxicity. Platinum(II) cis-diamine-1,1-cyclobutanedicarboxylate (hereinafter referred to as "CBDCA") and platinum(II) cis-diamine-O,O'-glycolate (see Japanese Unexamined Patent Publication No. 56-154,493, etc.) have been developed as a result of such studies and are regarded as the second generation of platinum antitumor agents.

These compounds do exhibit a reduced renal toxicity, compared with CDDP, but their anti-tumor activity is also reduced compared with that of CDDP. Therefore, platinum complexes having a high antitumor activity and a low toxicity must be developed.

SUMMARY OF THE INVENTION

The primary object of the present invention is to provide novel platinum(II) complexes having a potent antitumor activity and a low toxicity, and to provide pharmaceutical compositions for the treatment of malignant tumors.

In one aspect of the present invention, there is provided a platinum complex represented by the following general formula (A):

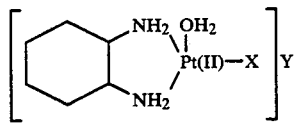

where X represents

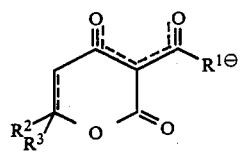

wherein $R^1$ is an alkyl group having 1 to 18 carbon atoms, an alkenyl group having 1 to 18 carbon atoms or a group $-(-Z-)-R^4$ in which Z represents $-CH=CH-$ or an alkylene group having 1 to 5 carbon atoms, and $R^4$ is a phenyl group, a hydroxyphenyl group, and alkoxyphenyl group having 7 to 12 carbon atoms, a halogenophenyl group, a nitrophenyl group, an alkoxycarbonylphenyl group having 8 to 13 carbon atoms, a cyclohexyl group having an alkyl substituent having 1 to 5 carbon atoms, or a group represented by the formula:

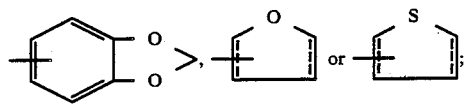

$R^2$ is a hydrogen atom or an alkyl group having 1 to 18 carbon atoms, $R^3$ is a hydrogen atom or an alkyl group having 1 to 3 carbon atoms, or $R^2$ and $R^3$ are linked together to form an alkylene group having 2 to 7 carbon atoms, with the proviso that when there is a 5,6-double bond, $R^3$ is not present; the dotted line indicates that the bond may be either a single bond or a double bond; the chain line indicates a conjugated system; the 1,2-diaminocyclohexane moiety has a cis-trans-l-or trans-d-configuration; and Y represents an anion.

In another aspect of the present invention, there is provided a pharmaceutical composition for the treatment of malignant tumors, comprising a therapeutically effective amount of a platinum complex represented by the general formula (A) and a pharmaceutically acceptable carrier therefor.

DESCRIPTION OF THE PREFERRED EMBODIMENTS

The platinum complexes of the present invention, represented by the general formula (A) has a ligand of 1,2-diaminocyclohexane and a ligand of a 3-acylpyran-2,4-dione derivative represented by the following general formula (B):

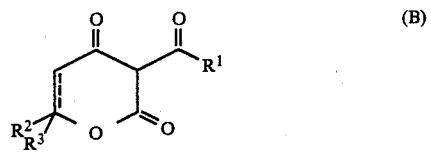

wherein $R^1$, $R^2$ and $R^3$ are as defined above. The latter ligand is coordinated in the form which is formed by removing one mole of proton from the compound of the formula (B) and which is represented by the following general formula (X):

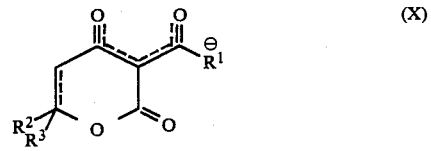

The ligand of the formula (X) indicates a conjugated system represented by the following formulae:

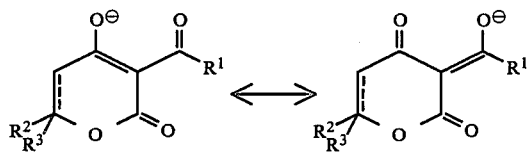

Among the compounds of the formula (A), those which have, in the formula (X), a methyl, 2-tetrahydrofurylethyl, 2-furylethyl, m-hydroxyphenylethyl, p-chlorophenylethyl or 3,4-methylenedioxyphenylethyl group as $R^1$, a methyl group as $R^2$, and a hydrogen atom as $R^3$ are preferable, although the compounds of the present invention are not limited thereto.

The anion Y in the compounds represented by the formula (A) may be either a univalent anion or a multivalent anion having a valency of two or more, but, is preferably a univalent anion. The univalent anion includes, for example, an aliphatic carboxylic acid ion having 1 to 10 carbon atoms such as $CH_3COO^-$ and $C_3H_7COO^-$, $NO_3^-$, a halogen ion and the anion of the formula (X).

The platinum complexes of the general formula (A) may be prepared according to one of the following reaction formulae.

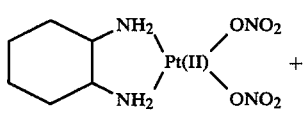

(C)

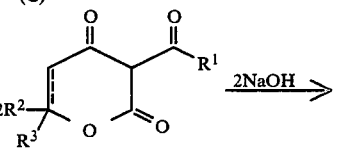

(B)

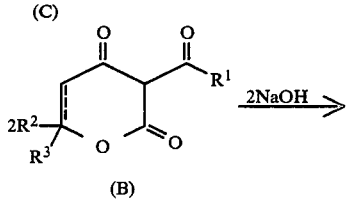

(A')

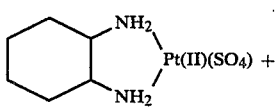

(D)

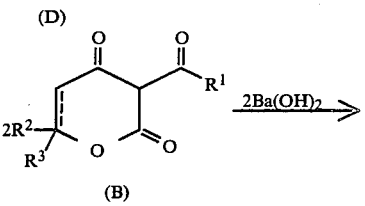

(B)

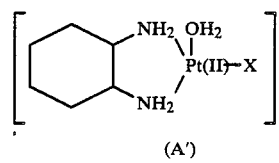

(A')

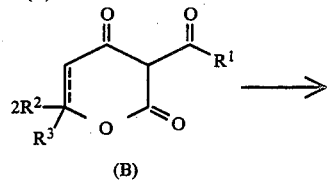

(E)

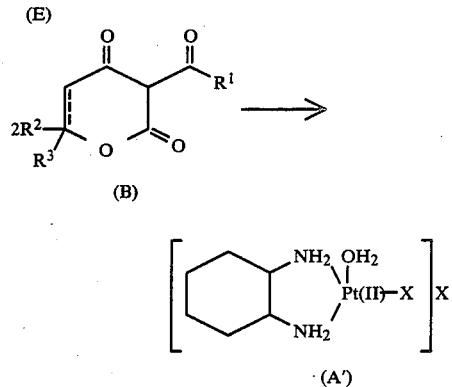

(A')

In the above-mentioned reaction formulae, $R^1$, $R^2$, $R^3$, and the dotted line are as defined above.

The reactions (1) and (2) can be conducted in the presence of an alkali metal hydroxide such as sodium hydroxide or potassium hydroxide, or an alkaline earth metal hydroxide such as barium hydroxide or calcium hydroxide. Of these, sodium hydroxide and potassium hydroxide are preferable in the reaction (1) and barium hydroxide is preferable in the reaction (2). Preferably, the amount of the alkali metal hydroxide in the reactions (1) and (2) is approximately twice the equivalent to the compound (B) and the amount of the alkaline earth metal hydroxide in the reactions (1) and (2) is approximately equivalent to the compound (B).

Compounds represented by the formula (A) wherein Y is an anion other than X can be prepared by reacting an acidic compound corresponding to the anion Y with the compound (A)'. For example, where the anion Y is a univalent anion, these compounds can be prepared according to the following reaction formula:

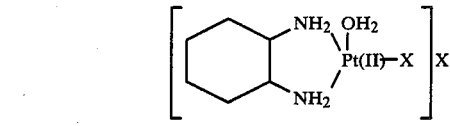

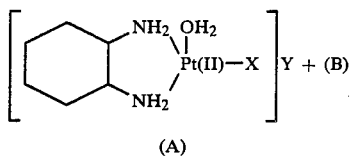

wherein Y represents an anion other than X. The above reaction (4) is an equilibrium reaction and the intended compound (A) can be selectively obtained by extracting the produced compound (B) with a solvent. As HY used in the above reaction (4), there can be mentioned, for example, an aliphatic carboxylic acid such as $CH_3COOH$ or $C_3H_7COOH$, $HNO_3$, or H.Hal (Hal represents a halogen).

The compounds (A) obtained by the reaction in an aqueous solution may be in the form of an aquo complex having coordinated water and such complexes are also included within the scope of the compounds of the present invention.

The compounds (C) and (D) used as the starting materials for the synthesis of the compounds of the present invention can be obtained by the reaction of a compound represented by the following formula (F):

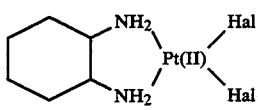
(F)

wherein Hal represents a halogen atom, with silver nitrate or silver sulfate, by utilizing a known technique, for example, the technique disclosed in Journal of Pharmaceutical Sciences, 65, 315 (1976).

The formula (F) indicates all the possible three isomers as to the dach moiety, that is, Pt(cis-dach)Hal$_2$, Pt(trans-l-dach)Hal$_2$ and Pt(trans-d-dach)Hal$_2$ according to the configuration of the used 1,2-diaminocyclohexane ("dach" indicates 1,2-diaminocyclohexane).

The compounds (E) are described in Cancer treatment Reports, vol. 61, P1519 (1977) and can be prepared by placing an aqueous solution of the compound (C) in contact with a strong anion exchange resin. The strong anion exchange resin includes, for example, Amberlite IRA-400 and Dia-ion SA-10A.

The compounds (B) are other starting compounds for the compounds of the present invention and can be synthesized according to the following processes disclosed in Japanese Unexamined Patent Publication No. 49-5,975 or Chemistry Letters, 1982, 1543–1546:

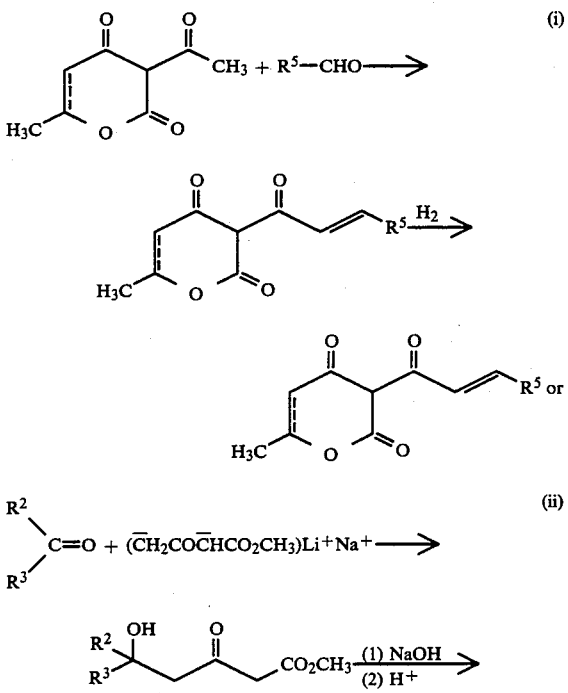

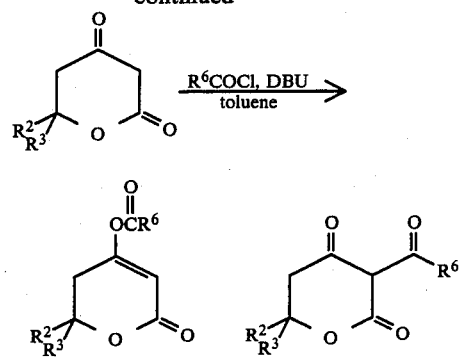

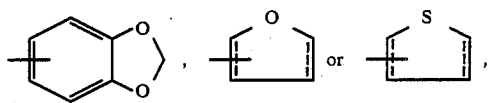

In the above reaction formulae (i) and (ii), $R^2$ and $R^3$ are as defined above; $R^5$ is an alkyl or alkenyl group having 1 to 16 carbon atoms, a phenyl group, a hydroxyphenyl group, an alkoxyphenyl group having 7 to 12 carbon atoms, a halogenophenyl group, a nitrophenyl group, an alkoxycarbonylphenyl group having 8 to 13 carbon atoms, a cyclohexyl group having an alkyl substituent having 1 to 5 carbon atoms, or a group represented by the formula:

and $R^6$ is an alkyl group having 1 to 18 carbon atoms or an aryl group.

The compounds of the present invention with a high antitumor activity and a low toxicity are useful for pharmaceutical compositions for the chemotherapy of malignant tumors. Furthermore, some of the platinum complexes of the present invention also exhibit a bacteriocidal activity, and thus are expected to be valuable for use as antimicrobial agents.

For chemotherapeutic use, the pharmaceutical composition comprising a therapeutically effective amount of at least one of the compounds of the present invention in conjunction or admixture with excipients or carriers may be administered in an oral or non-oral manner, preferably as tablets, coated tablets, pills, capsules, powders, troaches, liquid preparations, suppositories or injections. As the excipients or carriers, there can be mentioned lactose, sucrose, glucose, sorbitol, mannitol, potato starch, amilopectine, various other starches, cellulose derivatives such as carboxymethyl cellulose and hydroxyethyl cellulose, gelatin, magnesium stearate, polyvinyl alcohol, calcium stearate, polyethylene glycol wax, gum arabic, talc, titanium dioxide, vegetable oils such as olive oil, peanut oil and sesame oil, paraffin oil, neutral fat base, ethanol, propylene glycol, physiological saline solution, sterilized water, glycerol, a colorant, a taste-improving agent, a stabilizer, an isotonic agent, a buffering agent and other pharmaceutically acceptable excipients or carriers.

The pharmaceutical composition of the present invention contains at least one of the compounds of the present invention in an amount of 0.001 to 85% by weight, preferably 0.005 to 60% by weight, based on the weight of the composition.

Although the dose of the pharmaceutical composition of the present invention depends mainly on the conditions of the disease, the daily dose is generally 0.005 to 200 mg, preferably 0.01 to 50 mg, per kg of the body weight.

The present invention will now be described in detail with reference to the following examples.

EXAMPLE 1

[Pt(trans-l-1,2-diaminocyclohexane)](3-acetyl-6-methyltetrahydropyran-2,4-dione)$_2$.H$_2$O

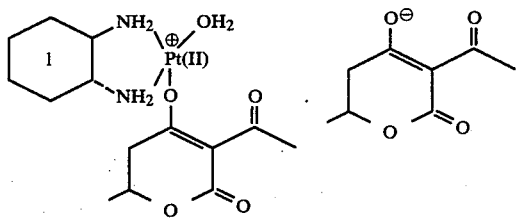

To 100 ml (4.2 millimoles) of an aqueous solution of [Pt(trans-l-dach)(OH)$_2$] ("dach" indicates 1,2-diaminocyclohexane) was added 1.72 g (10.1 millimoles) of 3-acetyl-6-methyltetrahydropyran-2,4-dione. The mixture was stirred at room temperature for 6 hours and thereafter concentrated to dryness at 45° to 50° C. The resulting solid was washed with ethyl acetate and dried at 40° to 45° C. under a reduced pressure to obtain 2.40 g of a light yellow complex (yield: 86%).

The melting point, elemental analytical data, and IR and NMR data of the obtained complex are as follows.

Melting point: 184° to 188° C. (with decomposition).

Elemental analysis as C$_{22}$H$_{34}$N$_2$O$_9$Pt: Calculated values: C=39.7%, H=5.15%, N=4.21%, Pt=29.31%. Found values: C=39.3%, H=4.9%, N=4.3%, Pt=28.0%.

IR (KBr) (cm$^{-1}$): 3420, 3200, 3080, 2980, 2940, 2860, 1700, 1660, 1620, 1570, 1390, 1290, 1260, 1060, 970, 770.

$^1$HNNR(d$_6$-DMSO) δ (ppm): 4.20 (m, 2H), 3.55 (s, 6H), 2.1-2.7 (m, 10H), 1.5-2.0 (m, 6H), 0.5-2.6 (m, 10H).

In the thus-prepared platinum complex, coordinated 3-acetyl-6-methyltetrahydropyran-2,4-dione and anionic 3-acetyl-6-methyltetrahydropyran-2,4-dione are present at a ratio of 1:1. This is seen from the fact that chemical shifts of the corresponding protons occur at the same intensities in different positions ($^1$HNMR, 400 MHz, D$_2$O).

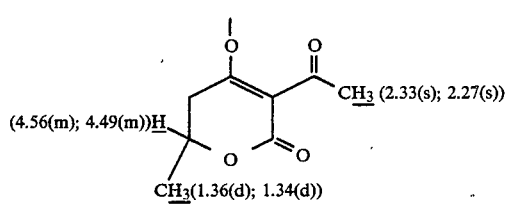

EXAMPLE 2

[Pt(trans-l-1,2-diaminocyclohexane)](3-acetyl-6-methyl-2H-pyran-2,4(3H)-dione)$_2$.H$_2$O

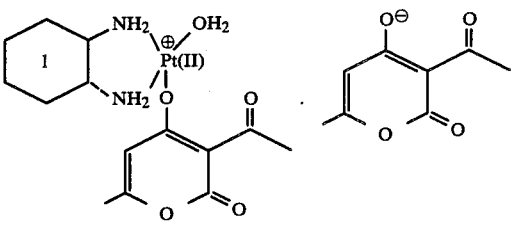

To 100 ml (4.2 millimoles) of an aqueous solution of [Pt(trans-l-dach)(OH)$_2$] was added a solution of 1.71 g (10.1 millimoles) of dehydroacetic acid in 25 ml of ethanol. The reaction and post treatment were carried out in a manner similar to those described in Example 1 to obtain 2.40 g (yield: 86%) of a light yellow complex.

The melting point, elemental analytical data and IR and NMR spectral data of the so-obtained complex are as follows.

Melting point: 191° to 196° C. (with decomposition).

Elemental analysis as C$_{22}$H$_{30}$N$_2$O$_9$Pt: Calculated values: C=39.94%, H=4.57%, N=4.23%, Pt=29.49%. Found values: C=39.2%, H=4.4%, N=4.5%, Pt=30.2%.

IR (KBr) (cm$^{-1}$): 3420, 3200, 3080, 2940, 2860, 1730, 1690, 1660, 1600, 1550, 1470, 1400, 1380, 1350, 1280, 1160, 1010.

$^1$HNMR (d$_6$-DMSO) δ (ppm) 5.99 (s, 1H), 5.39 (s, 1H), 3.48 (s, 6H), 2.32 (s, 3H), 2.25 (s, 3H), 2.05 (s, 3H), 1.91 (s, 3H), 0.5-2.6 (m, 10H).

In the thus-prepared platinum complex, coordinated 3-acetyl-6-methyl-2H-pyran-2,4(3H)-dione and anionic 3-acetyl-6-methyl-2H-pyran-2,4(3H)-dione are present at a ratio of 1:1. This is seen from the fact that chemical shifts of the corresponding protons occur at the same intensities in different positions ($^1$HNMR, 400 MHz, D$_2$O).

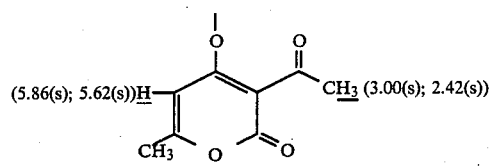

EXAMPLE 3

[Pt(trans-l-1,2-diaminocyclohexane)](3-acetyl-6-methyltetrahydropyran-2,4-dione)(CH$_3$COO).H$_2$O

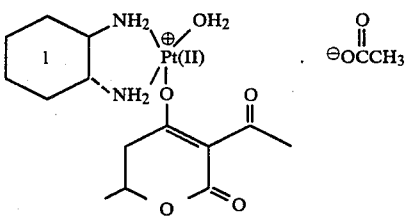

In 100 ml of water was dissolved 5.57 g (8.6 millimoles) of [Pt(trans-l-1,2-diaminocyclohexane)](3-acetyl-6-methyltetrahydropyran-2,4-dione)$_2$.H$_2$O prepared in Example 1, and 1.56 g (25.8 millimoles) of acetic acid was added. The mixture was stirred at room temperature for 3 hours, and the produced 3-acetyl-6-methyltetrahydropyran-2,4-dione was extracted four times with each 50 ml of ethyl acetate using a separating funnel. Water was distilled off from the residual aqueous layer under a reduced pressure by using a rotary evaporator, and the residue was evaporated to dryness under a reduced pressure by using a vacuum pump. To the thus-obtained solid was added 100 ml of ethyl acetate, and, while maintained at −10° C., the obtain product was pulverized and then washed. Thereafter, the powder was filtered and dried to obtain 4.25 g of a complex.

The melting point, elemental analytical data and IR and NMR spectral data of the obtained complex are as follows.

Melting point: 230° C. (non-melted and blakened).

Elementary analysis values as C$_{16}$H$_{28}$N$_2$O$_7$Pt: Calculated values: C=34.60%, H=5.08%, N=5.04%, Pt=35.12%. Found values: C=34.65%, H=5.01%, N=4.97%, Pt=35.3%.

IR (KBr) (cm$^{-1}$) 3400, 2925, 1702, 1560, 1440, 1420, 1390, 1250, 1075, 1060, 630, 520.

$^1$HNMR (D$_2$O) δ (ppm) 4.56 (m, 1H), 2.68–2.31 (m, 4H), 2.27 (s, 3H), 2.06 (2H), 1.93 (s, 3H), 1.60 (d, 2H), 1.38–1.33 (4H), 1.25–1.17 (m, 3H).

It is seen from $^1$NMR (400 MHz, D$_2$O) of the following formulae that one molecule of coordinated 3-acetyl-6-methyl-tetrahydropyran-2,4-dione and one molecule of acetic acid ion are present in the obtained complex.

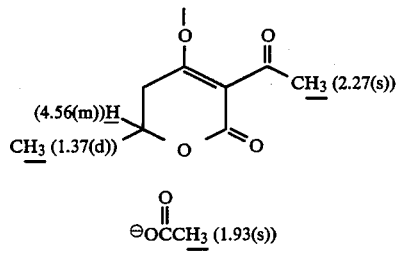

EXAMPLE 4

[Pt(trans-l-1,2-diaminocyclohexane)](3-acetyl-6-methyl-2H-pyran-2,4(3H)-dione)(CH$_3$COO).H$_2$O

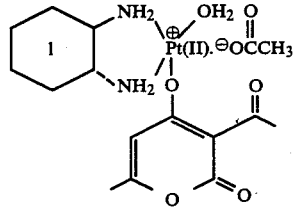

In 40 ml of water was dissolved 2.3 g (3.5 millimoles) of [Pt(trans-l-1,2-diaminocyclohexane)](3-acetyl-6-methyl-2H-pyran-2,4(3H)-dione)$_2$.H$_2$O prepared in Example 2, and 0.52 g (8.6 millimoles) of acetic acid was added. Using a separating funnel the reaction product was extracted with 20 ml of ethyl acetate. The aqueous layer was extracted twice with each 10 ml of ethyl acetate. Water was distilled off from the residual aqueous layer under a reduced pressure by using a rotary evaporator, and the residue was evaporated to dryness under a reduced pressure by using a vacuum pump. To the thus-obtained solid was added 50 ml of ethyl acetate, and, while maintained at −10° C., the obtain product was pulverized and then washed. Thereafter, the powder was filtered and dried to obtain 1.7 g of a complex.

The melting point, elemental analytical data and IR and NMR spectral data of the obtained complex are as follows.

Melting point: 250° C. (non-melted and blakened).

Elementary analysis values as C$_{16}$H$_{26}$N$_2$O$_7$Pt: Calculated values: C=34.72%, H=4.74%, N=5.06%, Pt=35.25%. Found values: C=34.43%, H=4.7%, N=5.21%, Pt=36.4%.

IR (KBr) (cm$^{-1}$): 3400, 2925, 1720, 1695, 1650, 1600, 1540, 1460, 1420, 1390, 1340, 1160, 1060, 1020, 1000, 970, 620, 540.

$^1$HNMR (D$_2$O) δ (ppm): 6.01 (s, 1H), 2.52–2.46 (2H), 2.41 (s, 3H), 2.09–1.97 (5H), 1.92 (s, 3H), 1.61–1.59 (2H), 1.34–1.24 (2H), 1.21–1.15 (2H).

It is seen from $^1$NMR (400 MHz, D$_2$O) of the following formulae that one molecule of coordinated 3-acetyl-6-methyl-2H-pyran-2,4(3H)-dione and one molecule of acetic acid are present in the obtained complex.

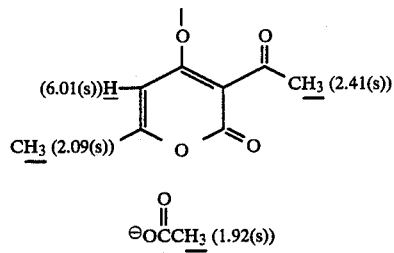

EXAMPLE 5

[Pt(trans-l-1,2-diaminocyclohexane)](3-acetyl-6-methyltetrahydropyran-2,4-dione) (C$_3$H$_7$COO).H$_2$O

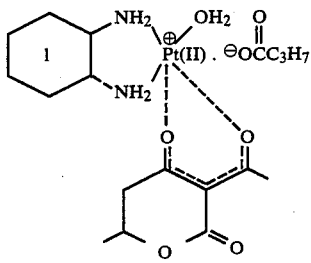

To 100 ml (4.2 millimoles) of an aqueous solution of Pt(trans-l-dach) (OH)$_2$ was added 0.37 g (4.2 millimoles) of butyric acid, and the mixture was stirred at room temperature for 2.5 hours. Then, 0.71 g (4.2 millimoles) of 3-acetyl-6-methyltetrahydropyran-2,4-dione was added to the mixture, and the mixture was stirred further for two days. The precipitated crystal was removed by filtration, and the filtrate was concentrated to dryness, washed with ethyl acetate and dried under a reduced pressure to obtain 1.7 g of a yellow complex (yield: 69%).

The melting point, elemental analytical data and IR spectral data of the obtained complex are shown below.

Melting point: 201° to 205° C. (with decomposition).

Elemental analysis values as $C_{18}H_{32}N_2O_7Pt$: Calculated values: C=37.1%, H=5.53%, N=4.80%, Pt=33.4%. Found values: C=36.5%, H=5.1%, N=4.8%, Pt=32.9%.

IR (KBr) (cm$^{-1}$) 3430, 3190, 3080, 2930, 1690, 1570, 1390, 1260, 1060, 970, 770, 520.

EXAMPLE 6

[Pt(trans-l-1,2-diaminocyclohexane)](3-(3-(2-tetrahydrofuryl)propionyl)-6-methyltetrahydropyran-2,4-dione)$_2$·H$_2$O

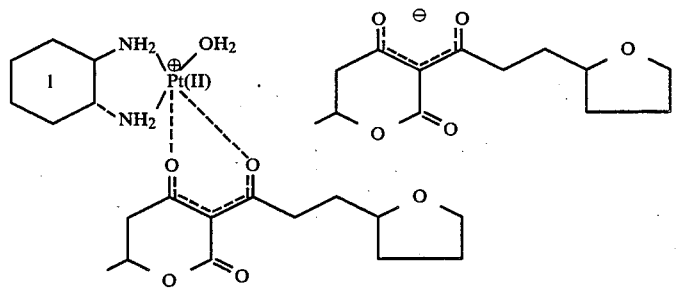

To 100 ml (4.2 millimoles) of an aqueous solution of [Pt(trans-l-dach) (OH)$_2$] was added a solution of 2.30 g (9.1 millimoles) of 3-(3-(2-tetrahydrofuryl)propionyl)-6-methyltetrahydropyran-2,4-dione, and the mixture was stirred at room temperature for 6 hours. Then, the reaction mixture was concentrated to dryness at a temperature of 45° to 50° C. The obtained solid was washed with ethyl acetate and dried under a reduced pressure at a temperature of 45° to 50° C. to obtain 2.80 g of a white complex (yield: 80%).

The melting point, elemental analytical data and IR and NMR spectral data of the so-obtained complex are as follows.

Melting point: 166° to 168° C. (with decomposition).

Elemental analysis values as $C_{32}H_{50}N_2O_{11}Pt$: Calculated values: C=46.09%, H=6.04%, N=3.36%, Pt=23.40%. Found values: C=45.7%, H=5.7%, N=3.5%, Pt=24.0%.

IR (KBr) (cm$^{-1}$): 3420, 3150, 3080, 2940, 2860, 1710, 1660, 1560, 1400, 1340, 1260, 1070.

$^1$HNMR (D$_2$O, 400 MHz) δ (ppm) 4.57 (m, 1H), 4.50 (m, 1H), 3.90 (m, 2H), 3.85 (m, 2H), 3.75 (m, 2H), 2.79 (m, 4H), 2.67 (d, 1H), 2.52 (m, 2H), 2.42 (d, 2H), 2.38 (m, 1H), 2.10 (m, 2H), 2.06 (m, 2H), 1.93 (m, 4H), 1.78–1.85 (m, 4H), 1.63 (m, 2H), 1.55 (m, 2H), 1.37 (m, 2H), 1.39 (d, 3H), 1.36 (d, 3H), 1.20 (m, 2H).

EXAMPLE 7

To 30 ml (3.2 millimoles) of an aqueous solution of Pt(trans-l-dach)SO$_4$ were added 1.61 g (6.4 millimoles) of 3-(3-(2-tetrahydrofuryl)propionyl)-6-methyltetrahydropyran-2,4-dione and 150 ml (3.2 millimoles) of an aqueous solution of Ba(OH)$_2$. The mixture was stirred at room temperature for 24 hours and concentrated at a temperature of 45° to 50° C. The precipitate (BaSO$_4$) was analytical data were 45.8% of C, 5.8% of H, 3.1% of N, and 22.9% of Pt.

EXAMPLE 8

[Pt(trans-l-1,2-diaminocyclohexane)](3-(3-(2-furyl)propionyl)-6-methyl-2H-pyran-2,4(3H)-dione)$_2$·H$_2$O

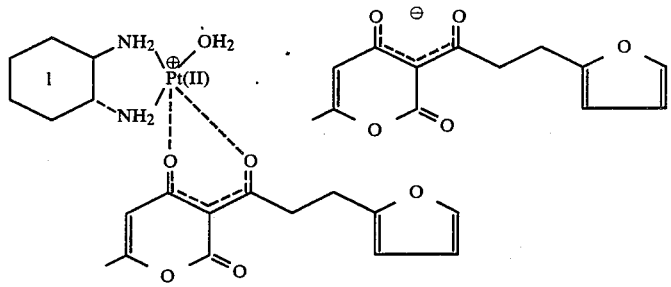

A solution of 1.30 g (5.2 millimoles) of 3-(3-(2-furyl)propionyl)-6-methyl-2H-pyran-2,4(3H)-dione in a mixed solvent of 10.7 ml of 1N NaOH and 30 ml of ethanol was added to 25 ml (5.3 millimoles) of an aqueous solution of [Pt(trans-l-dach) (H$_2$O)] (NO$_3$)$_2$. The mixture was stirred at room temperature for 2 hours. The precipitated crystal was collected by filtration, washed with water and then with ethyl acetate, and dried under a reduced pressure to obtain 0.91 g of a white complex (yield: 21%).

The melting point, elemental analytical data and IR spectral data of the obtained complex are as follows.

Melting Point: 204° to 207° C. (with decomposition).

Elemental analysis values as $C_{32}H_{36}N_2O_{10}Pt$: Calculated values: C=47.82%, H=4.51%, N=3.49%, Pt=24.27%. Found values: C=47.4%, H=4.4%, N=3.5%, Pt=24.9%.

IR (KBr) (cm$^{-1}$) 3420, 3160, 3090, 2940, 2860, 1730, 1680, 1660, 1550, 1420, 1160, 1010, 740.

EXAMPLE 9

[Pt(trans-l-1,2-diaminocyclohexane)](3-(3-(m-hydroxyphenyl)propionyl)-6-methyl-2H-pyran-2,4(3H)dione)₂.-H₂O

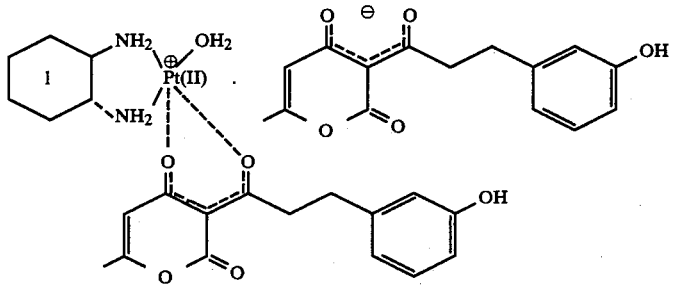

A solution of 1.23 g (4.5 millimoles) of 3-(3-m-hydroxyphenyl)propionyl-6-methyl-2H-pyran-2,4(3H)-dione in 65 ml of methanol, and 4.3 ml of 1N NaOH were added to 20 ml (2.1 millimoles) of an aqueous solution of [Pt(trans-l-dach) (H₂O)₂] (NO₃)₂. The mixture was stirred at room temperature for 20 hours, concentrated to 38 g and then added dropwise to 75 ml of water to precipitate a thick syrup-like substance. After removal of the supernatant formed, 150 ml of water was added to solidify the syrup-like substance while the mixture was stirred at room temperature for 2 hours. The solidified material was collected by filtration, washed with ethyl acetate and dried under a reduced pressure to obtain 1.20 g of a light-yellow crystal (yield: 65%).

The melting point, elemental analytical data and IR spectral data are as follows.

Melting point: 179° to 182° C. (with decomposition).
Elemental analysis values as $C_{36}H_{42}N_2O_{11}Pt$: Calculated values: C=49.48%, H=4.84%, N=3.21%, Pt=22.33%. Found values: C=49.8%, H=4.7%, N=3.1%, Pt=21.8%.

IR (KBr) (cm⁻¹) 3400, 3200, 3100, 2940, 2860, 1700, 1660, 1590, 1550, 1460, 1420, 1260, 1160, 1010.

EXAMPLE 10

[Pt(cis-1,2-diaminocyclohexane)](3-(3-(m-hydroxyphenyl)propionyl-6-methyl-2H-pyran-2,4(3H)-dione)₂.-H₂O A solution of 2.30 g (8.4 millimoles) of 3-(3-m-hydroxyphenyl)propionyl-6-methyl-2H-pyran-2,4(3H)-dione in a mixed solvent of 8.6 ml of 1N NaOH and 50 ml of water was added to a diluted solution of 20 ml (4.2 millimoles) of an aqueous solution of [Pt(cis-dach) (H₂O)₂] (NO₃)₂ with 30 ml of water. The mixture was stirred at room temperature for 2 hours. The precipitated crystal was collected by filtration, washed with water and then with ethyl acetate, and dried under a reduced pressure to obtain 1.80 g of a light-yellow complex (yield: 49%).

The melting point, elemental analytical data and IR and NMR spectral data of the obtained complex are as follows.

Melting point: 196° to 190° C. (with decomposition).
Elemental analysis values as $C_{36}H_{42}N_2O_{11}Pt$: Calculated values: C=49.48%, H=4.84%, N=3.21%, Pt=22.33%. Found values: C=49.7%, H=4.8%, N=3.2%, Pt=21.9%.

IR (KBr) (cm⁻¹): 3400, 3200, 3100, 2940, 2860, 1730, 1690, 1660, 1590, 1550, 1460, 1420, 1250, 1160, 1010, 780.

¹HNMR (d₆-DMSO) δ (ppm) 9.10 (br, 2H), 6.7–7.1 (m, 2H), 6.3–6.6 (m, 6H), 5.81 (s, 1H), 5.32 (s, 1H), 3.48 (br, 6H), 2.3–3.2 (m, 10H), 1.82–2.0 (m, 6H), 0.5–1.8 (m, 8H).

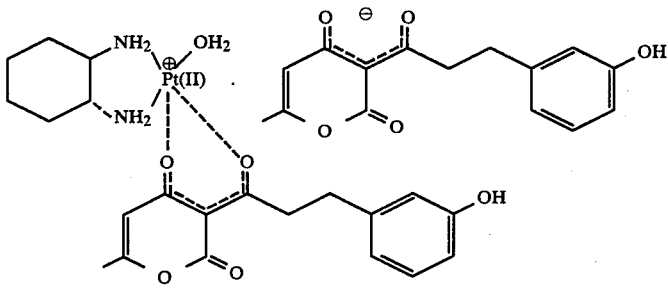

EXAMPLE 11

[Pt(trans-l-1,2-diaminocyclohexane)](3-(3-(p-chlorophenyl)propionyl-6-methyl-2H-pyran-2,4(3H)-dione)₂.-H₂O

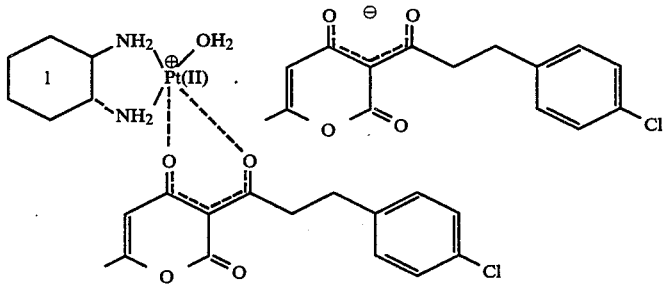

A solution of 2.12 g (7.2 millimoles) of 3-(3-p-chlorophenyl)propionyl-6-methyl-2H-pyran-2,4(3H)-dione in 200 ml of methanol was added to 15 ml of an aqueous solution of 3.2 millimoles of [Pt(trans-l-dach) (H₂O)₂]-(NO₃)₂, and then 7.2 ml of an aqueous solution of 1N-NaOH was added to the mixture. The mixture was stirred at room temperature for 20 hours. A mirror amount of a precipitate was removed by filtration and the filtrate was concentrated to 25 g. Then, 300 ml of water was added to the concentrate and the mixture was stirred at room temperature for 2 hours. The solidified material was collected by filtration, washed with ethyl acetate, and dried under a reduced pressure to obtain 1.75 g of a white complex (yield: 60%).

The melting point, elemental analytical data and IR spectral data of the obtained complex are as follows.

Melting point: 188° to 192° C. (with decomposition).

Elemental analysis values as $C_{36}H_{40}N_2O$ Pt: Calculated values: C=47.48%, H=4.43%, N=3.08%, Pt=21.42%. Found values: C=47.9%, H=4.3%, N=3.2%, Pt=20.8%.

IR (KBr) (cm$^{-1}$) 3420, 3160, 3080, 2940, 2860, 1730, 1690, 1660, 1610, 1550, 1510, 1490, 1420, 1090, 1010, 830.

EXAMPLE 12

[Pt(trans-l-1,2-diaminocyclohexane)]₅(3-(3-(3,4-methylene-dioxyphenyl)propionyl)-6-methyl-2H-pyran-2,4(3H)-dione)₂.H₂O

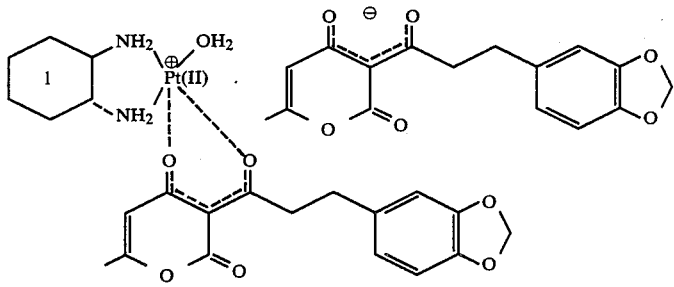

The procedure described in Example 11 was repeated using 2.21 g (7.3 millimoles) of 3-(3-(3,4-methylenedioxyphenyl)propionyl)-6-methyl-2H-pyran-2,4(3H)-dione in place of 3-(3-(p-chlorophenyl)propionyl-6-methyl-1-2H-pyran-2,4(3H)-dione, to obtain 2.25 g of a white complex (yield: 76%).

The melting point, elemental analytical data and IR spectral data of the obtained complex are as follows.

Melting point: 186° to 188° C. (with decomposition).

Elemental analysis values as $C_{38}H_{42}N_2O_{13}Pt$: Calculated values: C=49.09%, H=4.55%, N=3.01%, Pt=20.98%. Found values: C=49.2%, H=4.4%, N=3.2%, Pt=20.8%.

IR (KBr) (cm$^{-1}$) 3420, 3180, 3080, 2940, 1730, 1690, 1660, 1610, 1550, 1500, 1490, 1420, 1400, 1240, 1040, 920.

EXAMPLE 13

[Pt(trans-l-1,2-diaminocyclohexane)](3-acetyltetrahydropyran-2,4-dione)₂.H₂O

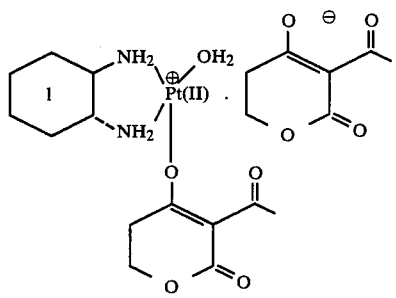

A solution of 1.56 g (10 millimoles) of 3-acetyltetrahydropyran-2,4-dione in 50 ml of ethanol was added to 60 ml (4.0 millimoles) of an aqueous solution of [Pt(trans-l-dach) (OH)₂] while being stirred under cooling with ice. The reaction mixture was allowed to stand at room temperature for 2 days and then concentrated to dryness under a reduced pressure in a water both maintained at 40° C. The resultant solid was incorporated with tetrahydrofuran, pulverized, washed, filtered and then dried at room temperature under a reduced pressure to obtain 2.30 g of a light yellow complex (yield: 90%).

The melting point, elemental analytical data and IR spectral data of the obtained complex are as follows.

Melting point: 200° C. (with decomposition).

Elemental analysis values as $C_{20}H_{30}N_2O_9Pt$: Calculated values: C=37.68%, H=4.74%, N=4.39%, Pt=30.60%. Found values: C=37.69%, H=4.60%, N=4.46%, Pt=30.94%.

IR (KBr) (cm$^{-1}$): 3400, 3062, 2940, 2368, 1688, 1570, 1390, 1270, 1187, 1102, 1023, 942, 915, 866, 775, 719.

$^1$HNMR (D$_2$O) δ (ppm): 4.29 (t, 2H), 4.24 (t, 2H), 2.58 (t, 2H), 2.50–2.47 (m, 4H), 2.32 (s, 3H), 2.57 (s, 3H), 2.07 (d, 2H), 1.63–1.55 (m, 2H), 1.40–1.31 (m, 2H), 1.23–1.12 (m, 2H).

EXAMPLE 14

[Pt(trans-l-1,2-diaminocyclohexane)](3-acetyl-6-methyl-2H-pyran-2,4(3H)-dione (NO$_3$).H$_2$O

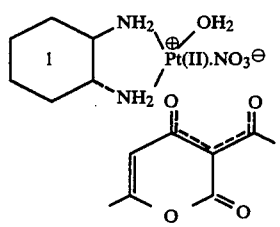

A solution of 2.12 g (12.6 millimoles) of dehydroacetic acid in 12.6 ml of a 1N aqueous solution of NaOH was added dropwise to 30 ml (6.3 millimoles) of an aqueous solution of [Pt(trans-l-dach) (H$_2$O)$_2$](NO$_3$)$_2$ at room temperature with stirring. Reaction was carried our for 20 hours. The precipitated crystal was collected by filtration, washed with water and ethyl acetate and dried at 40° to 45° C. under a reduced pressure to obtain 2.28 g of a white powdery complex (yield: 65%). The melting point, elemental analytical data and IR spectral data of the obtained complex are as follows.

Melting point: 195° to 198° C. (with decomposition).

Elemental analysis values as $C_{14}H_{23}N_3O_8Pt$: Calculated values: C=30.22%, H=4.17%, N=7.55%, Pt=35.06%. Found values: C=30.6%, H=3.8%, N=7.4%, Pt=32.8%.

IR (KBr) (cm$^{-1}$) 3440, 3200, 3100, 2940, 2860, 1760, 1730, 1710, 1660, 1550, 1470, 1430, 1380, 1170, 1070, 1030, 1010, 830.

EXAMPLE 15

Approximately 10$^5$ cells of mouse leukemia L1210 which had been subcultured in DBA/2 mice were inoculated into the abdominal cavity of CDF$_1$ mouse (male, 6 weeks old, each group consisting of 6 to 10 mice). A test platinum complex was administered intraperitoneally three times, that is, once on Day 1, on Day 5 and on Day 9, Day 0 being the day of inoculation. CDDP and CBDCA were tested as the positive control. Each complex tested was used in the form of a solution or suspension in 0.05% "Tween 80"-saline or in distilled water. Antitumor activity was evaluated based on the T/C value, calculated according to the following formula:

$$T/C\ (\%) = \frac{\text{average survival days of treated animals}}{\text{average survival days of control animals}} \times 100$$

The number of living mice was also recorded on the 30th day.

The results are shown in Table 1.

TABLE 1

Antitumor Activity of Platinum Complexes against L1210 Mouse Leukemia in Mice

| Compound | Dose (mg/kg) | Survival days (mean ± standard deviation) | T/C (%) | Survival rate |
|---|---|---|---|---|
| Control | — | 8.4 ± 1.0 | — | 0/10 |
| Compound of Example 1 | 1 | 8.5 ± 0.5 | 101 | 0/6 |
|  | 10 | 11.5 ± 1.2 | 137 | 0/6 |
|  | 25 | 14.2 ± 3.2 | 169 | 0/6 |
|  | 50 | 17.0 ± 3.0 | 202 | 0/6 |
|  | 100 | 15.5 ± 5.0 | 185 | 0/6 |
|  | 200 | 6.0 | 71 | 0/6 |
| Compound of Example 2 | 1 | 8.7 ± 0.5 | 104 | 0/6 |
|  | 10 | 13.8 ± 3.6 | 164 | 0/6 |
|  | 25 | 19.7 ± 7.5 | 235 | 1/6 |
|  | 50 | 10.0 ± 1.1 | 119 | 0/6 |
|  | 100 | 6.3 ± 2.0 | 75 | 0/6 |
|  | 200 | 2.8 ± 1.6 | 33 | 0/6 |
| CDDP | 2.5 | 15.2 ± 1.9 | 181 | 0/6 |
|  | 5.0 | 18.5 ± 6.0 | 220 | 1/6 |
|  | 7.5 | 17.0 ± 2.2 | 202 | 0/6 |
| Control | — | 8.4 ± 0.8 | — | 0/10 |
| Compound of Example 3 | 1 | 9.2 ± 1.0 | 110 | 0/6 |
|  | 5 | 12.8 ± 3.0 | 152 | 0/6 |
|  | 10 | 14.0 ± 2.6 | 167 | 0/6 |
|  | 25 | 23.0 ± 6.4 | 274 | 2/6 |
|  | 50 | 15.2 ± 4.1 | 181 | 0/6 |
|  | 100 | 7.7 ± 1.5 | 91 | 0/6 |
|  | 200 | 3.0 ± 2.0 | 36 | 0/6 |
| CDDP | 2.5 | 12.0 ± 3.0 | 143 | 0/6 |
|  | 5 | 14.3 ± 2.9 | 170 | 0/6 |
|  | 7.5 | 15.5 ± 2.1 | 185 | 0/6 |
| Control | — | 8.5 ± 1.2 | — | 0/6 |
| Compound of Example 5 | 1 | 8.8 ± 1.6 | 104 | 0/6 |
|  | 10 | 10.2 ± 1.6 | 120 | 0/6 |
|  | 25 | 11.8 ± 1.7 | 139 | 0/6 |
|  | 50 | 16.3 ± 5.0 | 192 | 0/6 |
|  | 100 | 14.2 ± 5.0 | 167 | 0/6 |
| CDDP | 2.5 | 13.0 ± 3.1 | 153 | 0/6 |
|  | 5 | 18.2 ± 0.4 | 214 | 0/6 |
|  | 7.5 | 20.2 ± 4.8 | 238 | 0/6 |
| Control | — | 8.4 ± 1.0 | — | 0/10 |
| Compound of Example 14 | 1 | 8.2 ± 0.4 | 98 | 0/6 |
|  | 10 | 11.3 ± 0.8 | 135 | 0/6 |
|  | 25 | 19.0 ± 8.5 | 226 | 2/6 |
|  | 50 | 18.0 ± 6.2 | 214 | 1/6 |
|  | 100 | 9.5 ± 1.2 | 113 | 0/6 |
|  | 200 | 5.0 | 60 | 0/6 |
| CDDP | 2.5 | 10.5 ± 1.8 | 125 | 0/6 |
|  | 5.0 | 15.5 ± 1.4 | 185 | 0/6 |
|  | 7.5 | 22.3 ± 3.9 | 266 | 1/6 |
| Control | — | 8.5 ± 0.5 | — | 0/10 |
| CBDCA | 1 | 8.3 ± 0.5 | 98 | 0/10 |
|  | 10 | 9.3 ± 0.5 | 109 | 0/10 |
|  | 25 | 10.1 ± 1.3 | 119 | 0/10 |
|  | 50 | 13.1 ± 2.3 | 156 | 0/10 |
|  | 100 | 14.1 ± 3.7 | 166 | 0/10 |
|  | 200 | 9.6 ± 0.7 | 113 | 0/10 |

EXAMPLE 16

The acute toxicity test of the compounds of the present invention to mice were carried out by using CDDP as the control. Platinum complexes to be tested was administered intraperitoneally to Slc:ICR mice (male, 5 weeks old, 6 mice/group). Each complex was used in the form of a solution or suspension in a 0.05% "Tween 80"-saline. The LD$_{50}$ value was calculated by the Miller-Tainter method from the death rate on the 14th day from the date of the administration. The results are shown in Table 2.

TABLE 2

| Compound | LD$_{50}$ Value (mg/kg) |
|---|---|
| CDDP | 15.3 |
| Compound of Example 1 | 98 |

TABLE 2-continued

| Compound | LD$_{50}$ Value (mg/kg) |
| --- | --- |
| Compound of Example 2 | 61 |
| Compound of Example 3 | 61 |
| Compound of Example 5 | 111 |
| Compound of Example 14 | 73 |

We claim:

1. A platinum complex represented by the following general formula (A):

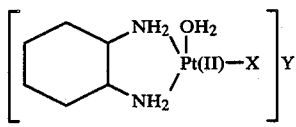

where X represents

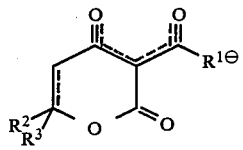

wherein R$^1$ is an alkyl group having 1 to 18 carbon atoms, an alkenyl group having up to 18 carbon atoms or a group —(Z)—R$^4$ in which Z represents —CH=CH— or an alkylene group having 1 to 5 carbon atoms, and R$^4$ is a phenyl group, a hydroxyphenyl group, an alkoxyphenyl group having 7 to 12 carbon atoms, a halogenophenyl group, a nitrophenyl group, an alkoxycarbonylphenyl group having 8 to 13 carbon atoms, a cyclohexyl group having an alkyl substituent having 1 to 5 carbon atoms, or a group represented by the formula:

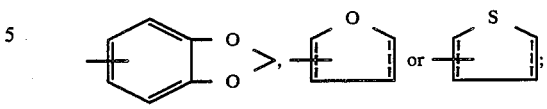

R$^2$ is a hydrogen atom or an alkyl group having 1 to 18 carbon atoms, R$^3$ is a hydrogen atom, or R$^2$ and R$^3$ are linked together to form an alkylene group having 2 to 7 carbon atoms, with the proviso that when there is a 5,6-double bond, R$^3$ is not present; the dotted line indicates that the bond may be either a single bond or a double bond; the chain line indicates a conjugated system; the 1,2-diaminocyclohexane moiety has a cis-, trans-l- or trans-d-configuration; and Y represents an anion.

2. A platinum complex of claim 1, wherein R$^1$ is a methyl, 2-tetrahydrofurylethyl, 2-furylethyl, m-hydroxyphenylethyl, p-chlorophenylethyl or 3,4-methylenedioxyphenylethyl group, R$^2$ is a methyl group, and R$^3$ is a hydrogen atom.

3. A platinum complex of claim 1, wherein Y is a univalent anion.

4. A platinum complex of claim 1, wherein Y is an anion selected from the group consisting of an aliphatic carboxylic acid ion having 1 to 10 carbon atoms, an NO$_3$ ion, a halogen ion and X (X has the same meaning as defined in claim 1).

5. A pharmaceutical composition for the treatment of malignant tumors, which comprises a therapeutically effective amount of a platinum complex represented by the general formula (A) of claim 1 and a pharmaceutically acceptable carrier therefor.

* * * * *

UNITED STATES PATENT AND TRADEMARK OFFICE
CERTIFICATE OF CORRECTION

PATENT NO. : 4,980,347

DATED : December 25, 1990

INVENTOR(S) : Masaji Ohno et al

It is certified that error appears in the above-identified patent and that said Letters Patent is hereby corrected as shown below:

In Column 14, line 33, delete "196°" and insert therefor --186°--.

Signed and Sealed this

Twenty-eighth Day of April, 1992

Attest:

HARRY F. MANBECK, JR.

*Attesting Officer*  *Commissioner of Patents and Trademarks*